(12) United States Patent
DeLeo

(10) Patent No.: US 6,276,931 B1
(45) Date of Patent: Aug. 21, 2001

(54) ORTHODONTIC BRACKET

(76) Inventor: David B DeLeo, Suite 2Q 71 East Ave., Norwalk, CT (US) 06850

( * ) Notice: Subject to any disclaimer, the term of this patent is extended or adjusted under 35 U.S.C. 154(b) by 0 days.

(21) Appl. No.: 09/687,663

(22) Filed: Oct. 13, 2000

Related U.S. Application Data

(63) Continuation-in-part of application No. 09/273,971, filed on Mar. 22, 1999.

(51) Int. Cl.[7] ................................................ A61C 3/00
(52) U.S. Cl. ................................. 433/9; 433/8; 433/10
(58) Field of Search ............................. 433/9, 8, 10, 16, 433/13, 14, 11

Primary Examiner—John J. Wilson
Assistant Examiner—Robyn Kieu Doan

(74) Attorney, Agent, or Firm—Patrick J. Walsh

(57) ABSTRACT

An orthodontic bracket for straightening a tooth, has a base member adapted for attachment to the tooth to be straightened, and has a pair of spaced-apart upstanding walls each of which is provided with a slot for receiving a brace arch wire. The upstanding walls have retainer means which are engageable with a retainer band to hold in place the arch wire. In one embodiment, one of the slots in one wall has a ridge or narrowed portion on its bottom surface, which portion is so located with respect to the side faces of the wall that it facilitates any required bending of the arch wire. The elastic arch wire that is associated with the bracket can be easily bent over the ridge or narrowed portion due to the increased height provided by the same, for the purpose of applying a rotating force to the tooth to which the bracket is attached. Other embodiments of the invention have various ridge or ridgelike formations in different orientations, to facilitate the bending of the arch wire to correct the positioning of the teeth.

12 Claims, 1 Drawing Sheet

ORTHODONTIC BRACKET

CROSS REFERENCE TO RELATED APPLICATION

This application is a C-I-P of Ser. No. 09/273,971 filed Mar. 22, 1999.

STATEMENT AS TO RIGHTS TO INVENTIONS MADE UNDER FEDERALLY-SPONSORED RESEARCH AND DEVELOPMENT

Research and development of the present invention and application have not been Federally-sponsored, and no rights are given under any Federal program.

BACKGROUND OF THE INVENTION

1. Field of the Invention

This invention relates generally to orthodontic brackets, and more particularly to brackets of the type intended to effect a rotation or positional adjustment of a tooth which is malpositioned or misaligned in a patient's mouth.

2. Description of the Related Art Including Information Diclosed Under 37 CFR §§1.97–1.99

The following references are hereby cited as being representative of some of the known prior art in the field to which the present invention pertains:

U.S. Pat. Nos.:
3,250,003 3,772,787 4,068,379 4,165,561 4,256,455 4,659,309 4,749,352 4,842,513 5,607,299

U.S. Pat. No. 3,250,003 shows a bracket 10 in FIGS. 2, 3 and 5, having a slot 20 in its wall for receiving an arch wire, wherein the bottom surfaces of the slot are flat or smooth and devoid of ridges, or ridgelike formations. This is a usual slot construction which can present difficulty when used with super-elastic arch wires due to its geometry.

U.S. Pat. No. 3,772,787 shows in FIG. 6 an orthodontic bracket 16 having a slot 19 which likewise has a smooth or flat bottom surface that is devoid of ridges or ridgelike surfaces, this being subject to the same limitations as the bracket 10 of the previous patent with regard to the slot bottom.

U.S. Pat. No. 4,068,379 shows brackets, as bracket 10 in FIG. 3 for example, where the wall slots have bottom surfaces that are flat and devoid of ridges. Here, again, with the use of super-elastic arch wires, the manipulation or bending of the wires was not especially easy in order to effect the desired adjustment. A similar bracket is also shown in U.S. Pat. No. 4,165,561, FIGS. 1–3, having the same drawbacks just mentioned.

In U.S. Pat. No. 4,256,455 the orthodontic bracket shown in FIGS. 1–3 reveals slotted walls wherein the slots have smooth bottom faces. 2. The same problems exist here with respect to the forming of super elastic wires for the purpose of effecting corrective rotative adjustment of the teeth.

FIG. 9 of U.S. Pat. No. 4,659,309 reveals slotted walls of orthodontic brackets, but the slots that are shown all have smooth bottom walls or faces, being subject to the above drawbacks when super-elastic wires are being used for the adjustment of the tooth position.

In U.S. Pat. No. 4,749,352 the bracket 10 of FIGS. 1 and 2 has slotted walls, again with smooth bottom surfaces that are devoid of ridges or ridgelike formations. Manipulation of arch wires is subject to the same limitations as with the brackets mentioned above.

FIGS. 3–6 of U.S. Pat. No. 4,842,513 reveal brackets of various shapes and configurations, but each with slots that have smooth bottom surfaces which are not especially helpful in the manipulation of the arch wire.

U.S. Pat. No. 5,607,299 shows brackets in FIGS. 10 and 12 which are provided with grooves in the slots of the walls, for the purpose of reducing friction with the arch wires, and to provide a positioning means for a gauge that is used to form the arch wire. However, no mention is made of ridges or ridgelike formations to facilitate the bending of super elastic arch wires that are placed in the slots in unbent condition.

In the accompanying drawings, showing several embodiments of the invention:

Figure 3:
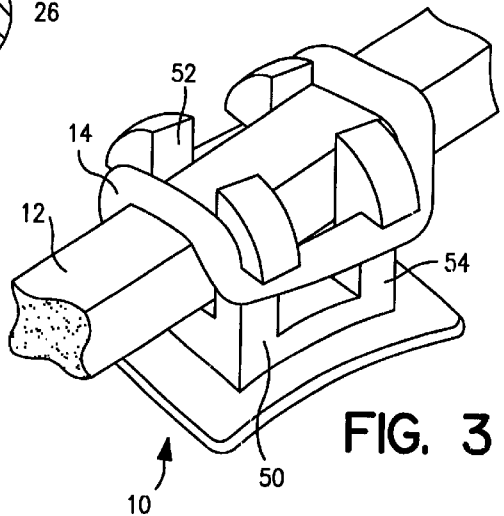
FIG. 3 is a perspective view of an assemblage of the bracket of FIG. 2 and a straight brace arch wire that is secured by an elastic band retainer, showing the application of the invention wherein an opposite tilt is being applied to a tooth, as compared to the tilt applied to the right-most tooth in the showing of FIG. 1.

As above mentioned, the present invention relates essentially to straight wire overcorrection brackets such as are used in correcting the tilt of a tooth in the mouth. One such bracket 10 is shown per se in FIG. 2, and a straight wire brace or arch wire 12 is shown in FIG. 3, as being attached to the overcorrection bracket 10 by an elastic band retainer 14.

Generally speaking, since the inception of orthodontics a recurring problem has been that of chronic relapse of a straightened tooth which was initially rotated to a position wherein it was orthodontically corrected. For example, if a mal-positioned or misaligned tooth were to be initially rotated to its orthodontically correct position in the mouth, it always had a tendency to return to its original, uneven position. The more severely the tooth had been rotated or corrected, the more tendency there was for the tooth to again misalign.

The main problem with trying to achieve over correction of a tilted or rotated tooth by means of a bracket that has a double flat bottom was that the amount of overcorrection was at best minimal.

Orthodontists have attempted to counter this problem by placing bends in arch wires so as to "overcorrect" the tooth and have also devised more or less elaborate retention strategies to meet the problem.

About the year 1979 a new development was devised, called a "straight wire concept", whereby it was no longer necessary for an orthodontist to place bends in the arch wires so as to achieve the proper adjusted position of a tooth, this being accomplished essentially wholly by a modification of the geometry of the bracket itself. The result was the creation of a series of brackets that had "tailored geometries", so to speak, whereby a selection of one particular bracket could satisfy several different situations.

Following this development and with the advent of super elastic wires, it was now theoretically almost impossible to put in place overcorrective bends with their attendant handicaps, in the arch wires that were used to apply pressure to the brackets attached to the teeth. However, remnants of the problem still existed, probably due to the impossibility to produce a line of brackets that would meet all of the conditions encountered in actual practice. And, as well, the super elastic wires now available could not be satisfactorally reformed when used with the "tailored" brackets, due to difficulties in reshaping this type of wire.

In solving this further problem I have now found that another change can now be made in the geometry of the overcorrection bracket, by which an advantageous cooperation or bending between the bracket and the straight arch wire is possible, thereby to enable the arch wire to be oriented or adjusted in conjunction with the bracket to now readily effect the carrying out of the desired tooth-rotation function.

With the new geometry as provided by this invention over correction can be more easily accomplished, the degree of overcorrection is increased by several fold.

Figure 1:
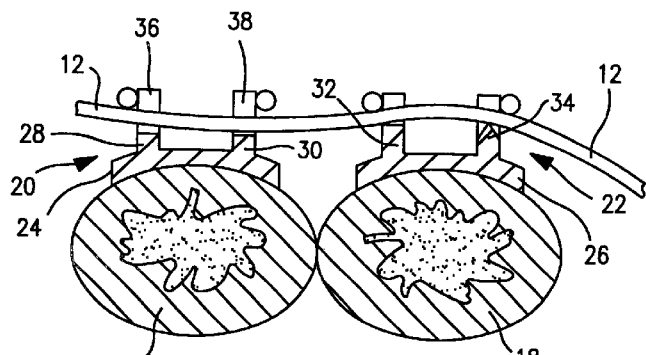
FIG. 1 is a horizontal sectional view of two adjoining teeth in the mouth of a patient, having secured to them two brackets one of which is made in accordance with the invention.

Accordingly and referring first to FIG. 1, two adjoining teeth 16 and 18 are shown, having attached to them overcorrection brackets 20 and 22 respectively. The brackets 20 and 22 have base members 24 and 26, from which pairs of upstanding walls 28, 30 and 32, 34 extend.

Figure 4:
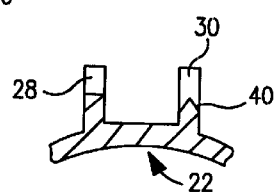
FIG. 4 is a fragmentary vertical section view per se of the right-most bracket of FIG. 1.

FIG. 4 shows the bracket 22 in section, standing by itself. The bracket 20 of FIG. 1 does not incorporate the present invention. It is seen to have slots 36 and 38 in its walls 28 and 30, which slots have flat bottom surfaces that are in the same plane relative to one another. At the bracket 20 the arch wire 12 is essentially straight, as it is intended to be.

However, in accordance with the invention and as seen in FIGS. 1 and 4, the arch wire 12 has a curvature that intentionally causes a shift of the tooth 18, bringing it into proper tooth rotation.

This is due to the fact that one of the slots of the bracket 22 has a ridge 40 on its bottom face, which enables a bend to be readily put in the elastic arch wire. In FIGS. 1 and 4 the slot 28 of the bracket 22 is shown as having a flat (high) bottom surface on average being twice the average height of the slot 30 having the ridge 40, whereas the slot 30 of the bracket has a lesser average height because its bottom is lower while it also has the ridge 40 over which the arch wire 14 can be readily bend in a desired manner to provide the proper position and orientation to the tooth 18.

Figure 5:
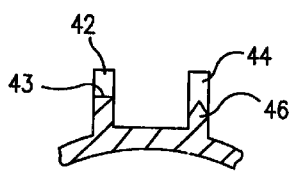
FIG. 5 is a fragmentary vertical section view somewhat similar to that of FIG. 4 except that its configuration applies a somewhat different rotation to the tooth to which the bracket may be applied.

A variation of this arrangement is shown in FIG. 5. In this figure the slots 42 and 44 have equal average depths, but the slot 44 has a ridge 46 to facilitate bending the arch wire 12 over it. The slot 42 has a flat bottom surface 43. I have found that bending a wire over or around a ridge formation, especially when using a straight super elastic wire such as is generally used at the present time, is more easily accomplished when the bracket slot has a ridged or narrowed bottom surface as compared with a slot having a flat bottom surface.

Figure 2:
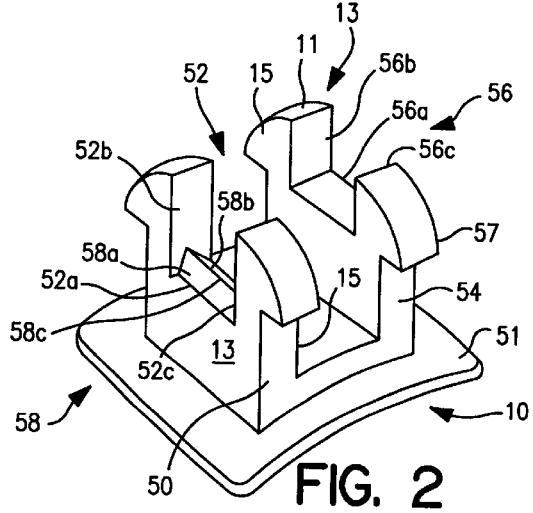
FIG. 2 is a perspective view of an improved bracket of the type shown in FIG. 1, but illustrating a modification of the invention wherein a left wall portion has a slot with a ridged bottom surface which is at a still lower level than the companion bottom surface of the slot in the adjoining wall surface of the bracket.

FIG. 2 shows more clearly that modification of the invention wherein the bracket 10 is similar to the bracket 10 of FIG. 3, in that the wall 50 has a slot 52 of deeper average depth than the slot in the wall 54 whose slot 56 is relatively shallow. The deep slot 52 has a bottom surface provided with a ridge 58 to facilitate the bending of the arch wire 12 thereover, for effecting rotation of a tooth.

Figure 6:
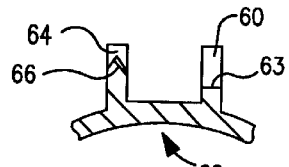
FIG. 6 is a fragmentary vertical section view like those of FIGS. 4 and 5 but showing still another embodiment of the invention.

In the modification shown in FIG. 6 the slot 60 of the bracket 62 has a low flat bottom surface 63 that is devoid of any ridges, and the slot 64 has a high bottom surface that is provided with a ridge 66. As with other embodiments, I have found that the simple provision of a ridge or narrow portion on the slot bottom surface enables the required wire adjustment to be made for facilitating tooth straightening or rotation process, saving considerable time both for the patient and the practicing dentist or orthodontist.

Figure 7:
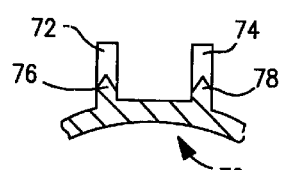
FIG. 7 is sectional view of a modified form of bracket according to the invention, wherein double ridges are provided for facilitating the bending of the arch wire to effect the desired tooth correction or rotation, one ridge being disposed in each upstanding wall portion.

In the embodiment of FIG. 7, the bracket 70 having the deep slots 72 and 74, has peaks or ridges 76 and 78 which are at approximately the same level and set deeply in the slots 72 and 74.

Figure 8:
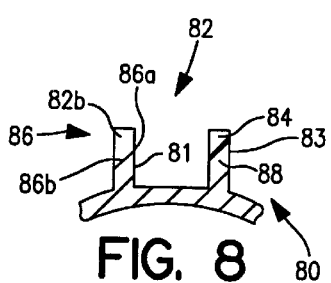
FIG. 8 is a sectional view of the present improved bracket wherein the ridges are offset outwardly and inwardly in the upstanding walls.

Another embodiment of the invention is shown in FIG. 8, wherein the bracket 80 having slots 82 and 84 in its walls is also provided with ridges 86 and 88 that are juxtaposed respectively to the inner and outer side surfaces of the bracket walls. This arrangement is effective where appreciable bending of the arch wire is involved. Also, the ridge 86 is lower than ridge 88 whereby an advantage is had in adapting the bracket to the particular environment surrounding the tooth that is to be rotated.

Figure 9:
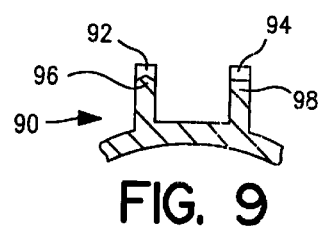
FIG. 9 is a sectional view of another modified form of bracket, wherein a ridge in the slot is rounded.

FIG. 9 illustrates another embodiment of the invention, wherein the bracket 90 has a slot 92 whose bottom wall is rounded at 96, whereas the bottom wall of the slot 94 can be flat to suit the conditions involved with the tooth.

Figure 10:
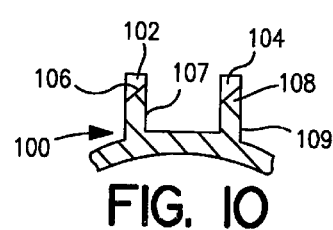
FIG. 10 is a sectional view of still another bracket made in accordance with the invention, wherein the outwardly and inwardly offset ridges in the walls are at the same level.

In FIG. 10 a bracket 100 has slots 102 and 104 whose bottom surfaces have ridges 106 and 108 respectively which are at the same level, and juxtaposed to the inner side surface 107 (ridge 106) and the outer side surface 109 (ridge 108) of the bracket walls. This type of bracket finds use in special situations where space requirements become a factor.

In each of the embodiments of FIGS. 1–10, the orthodontic bracket (as shown typically in FIG. 2) is characterized by a base member 51 with spaced apart upstanding walls 50, 54 having top 11, outer 13, and inner side surfaces 15. The walls have slots 52, 56 with each slot being open through the top wall 11 and defined by slot bottom surface 52a, 56a, and by slot confronting surfaces 52b–c, 56b–c. The slots are aligned for receiving an arch wire 12 (FIG. 3). Shoulders 57 extend from opposite sides of each wall and comprise a set of four shoulders for anchoring the elastic band retainer 14 for the arch wire.

The ridge 58 of FIG. 2 is formed by converging plane panels 58a–b situated on the slot bottom surface 52a between slot confronting surfaces 52b–c with the panels defining a ridge line 58c located intermediate the wall outer 13 and inner 15 side surfaces. The ridges 34, 40, 46, 76, and 78 of FIGS. 1, and 4 through 7 respectively are the same as ridge 58.

In FIG. 8, the ridge 86 is formed in slot 82 by inclined plane panel 86b defining the slot bottom surface between slot confronting surfaces 82b and (82c not shown) with the panel defining a ridge line 86a lying juxtaposed the wall inner side surface 81. The ridge 88 is similar to ridge 86, however it is juxtaposed outer wall surface 83.

The ridge 96 of FIG. 9 is formed by a rounded surface 96a situated on the slot bottom surface 92a between slot confronting surfaces 92b–c with the rounded surface defining a ridge located intermediate the wall outer 93 and inner 95 side surfaces.

In this way, in each embodiment of the invention an arch wire extending through aligned bracket slots can be bent over a ridged bottom surface to achieve tooth rotation.

It will now be seen that the various embodiments of the invention as illustrated and described herein fill the voids that existed in the prior art due to the development of the "so-called" straight-wire overcorrection bracket and superelastic wire provided therewith, and easily enable precise adjustments to be made in the art of orthodontia which heretofore were not possible in the straightening of mal=positioned or misaligned teeth.

Variations and modifications are possible without departing from the spirit of the invention.

Each and every one of the appended claims defines an aspect of the invention which is separate and distinct from all others, and accordingly it is intended that each claim be treated in this manner when examined in the light of the prior art devices in any determination of novelty or validity.

I claim:

1. An orthodontic bracket for cooperating with an arch wire for straightening a tooth comprising a base member adapted for attachment to a tooth to be straightened, the base member having a pair of spaced apart upstanding walls with each wall having outer and inner side surfaces, each wall having a slot for receiving a brace arch wire extending through the slots, each slot having a bottom surface, the slot of one of the walls having a ridge situated on the slot bottom surface between the outer and inner side surfaces of said one wall, the ridge formed by at least one panel defining a ridge line so that the arch wire can be bent over the ridge to apply a tilting force to the tooth to which the bracket is attached.

2. An orthodontic bracket for cooperating with an arch wire for straightening a tooth comprising a base member adapted for attachment to a tooth to be straightened, the base member having a pair of spaced apart upstanding walls with each wall having a slot for receiving a brace arch wire, each slot being defined by a bottom surface and slot confronting surfaces formed in each wall, the bottom surface of one of said slots being flat between the confronting surfaces of said one slot, and the bottom surface of the other of said slots being a ridge extending between the confronting surfaces of said other slot, the ridge formed by at least one panel defining a ridge line so that the arch wire extending through the slots can be bent over the ridge to apply a tilting force to the tooth to which the bracket is attached.

3. An orthodontic bracket for cooperating with an arch wire for straightening a tooth comprising a base member adapted for attachment to a tooth to be straightened, the base member having a pair of spaced apart upstanding walls with each wall having a slot for receiving a brace arch wire, each slot being defined by a bottom surface and slot confronting surfaces formed in each wall, the bottom surface of one of said slots being flat between the confronting surfaces of said one slot, the bottom surface of the other of said slots being a ridge extending between the confronting surfaces of said other slot, the ridge formed by at least one panel defining a ridge line and the average depth of the one and the other slots being substantially equal so that the arch wire extending through the slots can be bent over the ridge to apply a tilting force to the tooth to which the bracket is attached.

4. An orthodontic bracket for cooperating with an arch wire for straightening a tooth comprising a base member adapted for attachment to a tooth to be straightened, the base member having a pair of spaced apart upstanding walls with each wall having a slot for receiving a brace arch wire, each slot being defined by a bottom surface and slot confronting surfaces formed in each wall, the bottom surface of one of said slots being flat between the confronting surfaces of said one slot, the bottom surface of the other of said slots being a ridge extending between the confronting surfaces of said other slot, the ridge formed by at least one panel defining a ridge line and the average depth of the one slot being greater that the average depth of the other slot so that the arch wire extending through the slots can be bent over the ridge to apply a tilting force to the tooth to which the bracket is attached.

5. An orthodontic bracket for cooperating with an arch wire for straightening a tooth comprising a base member adapted for attachment to a tooth to be straightened, the base member having a pair of spaced apart upstanding walls with each wall having a slot for receiving a brace arch wire, each slot being defined by a bottom surface and slot confronting surfaces formed in each wall, the bottom surface of one of said slots being flat between the confronting surfaces of said one slot, the bottom surface of the other of said slots being a ridge extending between the confronting surfaces of said other slot, the ridge formed by at least one panel defining a ridge line and the average depth of the one slot being less that the average depth of the other slot so that the arch wire extending through the slots can be bent over the ridge to apply a tilting force to the tooth to which the bracket is attached.

6. An orthodontic bracket for cooperating with an arch wire for straightening a tooth comprising a base member adapted for attachment to a tooth to be straightened, the base member having a pair of spaced apart upstanding walls having outer and inner faces, each wall having a slot for receiving a brace arch wire, each slot being defined by a bottom surface and slot confronting surfaces formed in each wall, and the bottom surface of each of said slots having a ridge extending between the confronting surfaces of said slot each ridge formed by at least one panel defining a ridge line so that the arch wire can be bent over the ridge to apply a tilting force to the tooth to which the bracket is attached.

7. An orthodontic bracket as defined in claim 6 in which the ridges are juxtaposed the outer faces of the walls.

8. An orthodontic bracket for cooperating with an arch wire for straightening a tooth comprising a base member adapted for attachment to a tooth to be straightened, the base member having a pair of spaced apart upstanding walls with each wall having a slot for receiving a brace arch wire, each slot being defined by a bottom surface and slot confronting surfaces formed in each wall, the bottom surface of each of said slots having a ridge extending between the confronting surfaces of said slot, each ridge formed by at least one panel defining a ridge line and the average depth of the slots being substantially equal so that the arch wire can be bent over the ridges to apply a tilting force to the tooth to which the bracket is attached.

9. An orthodontic bracket for cooperating with an arch wire for straightening a tooth comprising a base member adapted for attachment to a tooth to be straightened, the base member having a pair of spaced apart upstanding walls having outer and inner faces, each wall having a slot for receiving a brace arch wire, each slot being defined by a bottom surface and slot confronting surfaces formed in each wall, the bottom surface of each of said slots having a ridge extending between the confronting surfaces of said slot, the ridge formed by at least one panel defining a ridge line and the average depth of one of said slots being greater that that of the other slot so that the arch wire can be bent over the ridges to apply a tilting force to the tooth to which the bracket is attached.

10. An orthodontic bracket as defined in claim 9 in which the ridges are juxtaposed the outer faces of the walls.

11. An orthodontic bracket for cooperating with an arch wire for straightening a tooth comprising a base member adapted for attachment to a tooth to be straightened, the base member having a pair of spaced apart upstanding walls with each wall having outer and inner side surfaces, each wall having a slot for receiving a brace arch wire extending through the slots, each slot having a bottom surface, the slot of one of the walls having a ridge formed on the slot bottom surface lying juxtaposed the outer side surface of said one wall, the ridge formed by a panel defining a ridge line so that the arch wire can be bent over the ridge to apply a tilting force to the tooth to which the bracket is attached.

12. An orthodontic bracket for cooperating with an arch wire for straightening a tooth comprising a base member adapted for attachment to a tooth to be straightened, the base member having a pair of spaced apart upstanding walls with each wall having outer and inner side surfaces, each wall having a slot for receiving a brace arch wire extending through the slots, each slot having a bottom surface, the slot of one of the walls having a ridge formed on the slot bottom surface lying juxtaposed the inner side surface of said one wall, the ridge formed by a panel defining a ridge line so that the arch wire can be bent over the ridge to apply a tilting force to the tooth to which the bracket is attached.

\* \* \* \* \*